United States Patent [19]

Thomas, Jr.

[11] Patent Number: 4,934,998
[45] Date of Patent: Jun. 19, 1990

[54] PRENATAL AUDIO APPARATUS

[76] Inventor: W. Shannon Thomas, Jr., P.O. Box 286, Orlando, Fla. 32802

[21] Appl. No.: 884,026

[22] Filed: Jul. 10, 1986

[51] Int. Cl.$^5$ .............................................. A61B 19/00
[52] U.S. Cl. .................................................... 600/27
[58] Field of Search ..................... 128/1 R, 1 C, 24 R; 434/250, 122, 266; 600/26-28

[56] References Cited

U.S. PATENT DOCUMENTS

| | | | |
|---|---|---|---|
| 3,908,634 | 9/1975 | Monaghan | 128/1 R |
| 3,994,282 | 11/1976 | Moulet | 128/1 C |
| 4,026,278 | 5/1977 | Ricketts et al. | 128/418 |
| 4,382,793 | 5/1983 | Anderson | 434/250 X |

FOREIGN PATENT DOCUMENTS 2339255 3/1979 France ................................ 128/1 C

*Primary Examiner*—Max Hindenburg
*Assistant Examiner*—J. P. Lacyk
*Attorney, Agent, or Firm*—William M. Hobby, III

[57] ABSTRACT

Prenatal audio apparatus includes a belt for fitting over a pregnant woman for directing audio sounds to the unborn baby. A belt has an inside surface, to fit against a pregnant woman's body, and an outside surface. Belt fasteners, such as hook and loop material, may adjustably attach the belt to the person. The belt can be made of a soft loop material fastenable for a hook material fastener portion. An audio signal source, such as a small portable tape recorder, is attachable to the belt. A pair of audio transducers are mounted in the belt in foam material with the output of the transducers facing the belt's inside surface, so that when attached to the patient, the sounds will be directed toward the unborn baby. The audio transducer is operatively connected to the audio signal source. The audio signal source may also be connected to earphones worn by the woman carrying the baby.

7 Claims, 1 Drawing Sheet

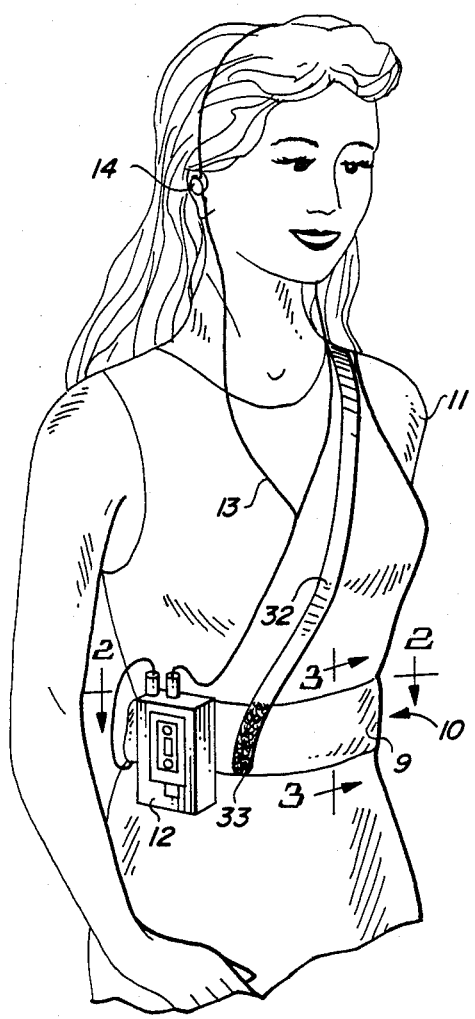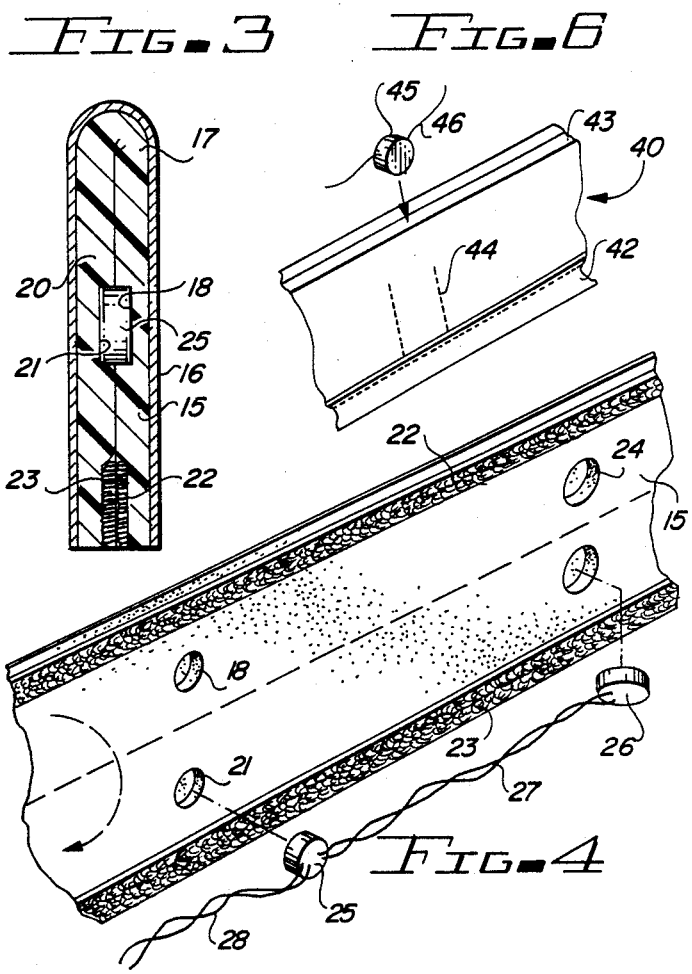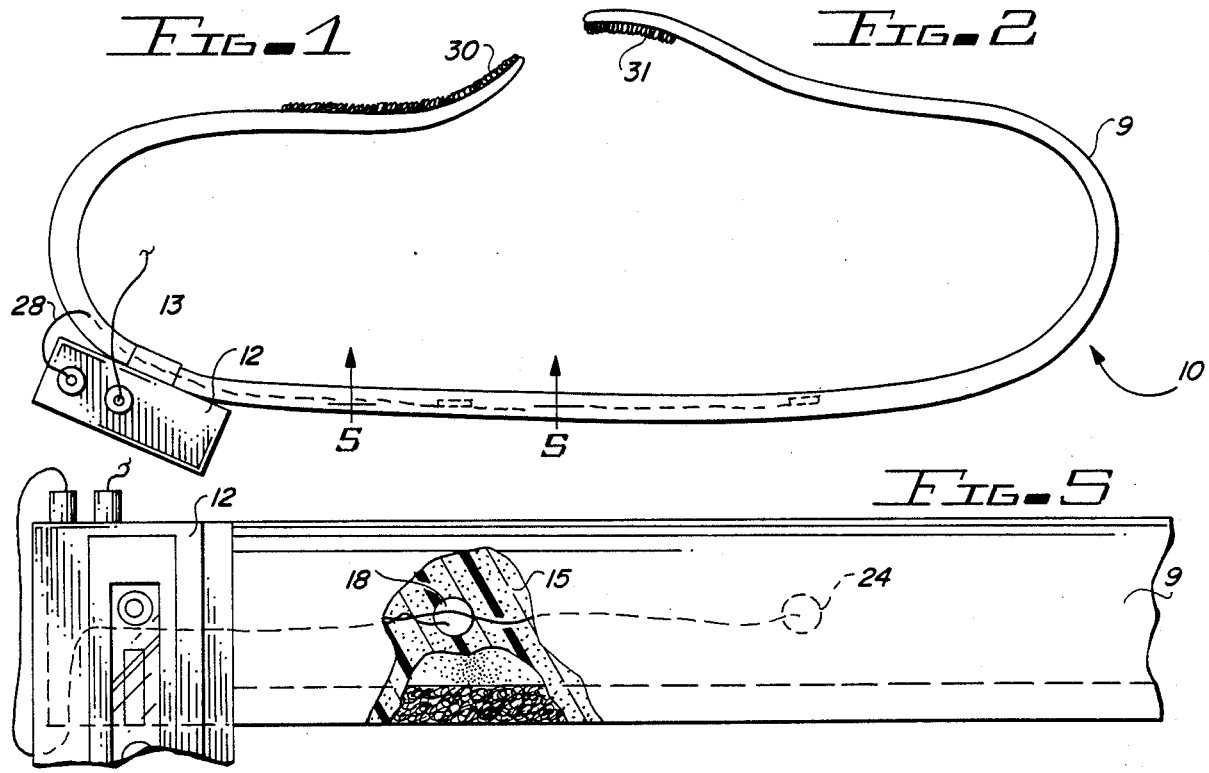

PRENATAL AUDIO APPARATUS

BACKGROUND OF THE INVENTION

The present invention relates to a prenatal audio apparatus and especially to a belt having audio transducers mounted thereto and connected to a portable tape recorder for directing sound to an unborn baby.

Research in recent years has indicated that an unborn fetus, while still being carried by a woman, has operative sense organs for a period time prior to the birth of the baby. One of the sense organs of the fetus is hearing. The baby, even though unborn, can hear certain sounds. The present invention directs predetermined music and other sound towards the fetus while simultaneously directing the music, or other audio material, to the mothers. Preselected audio material or music, for instance, can be used for calming an otherwise active fetus as well as used in certain prenatal learning techniques. Parents can also make their own tapes using their voices to familiarize the unborn baby with the parent's voices.

The prior art has included a variety of devices for attaching to a persons and a variety of belts for attaching around patients for different purposes. One such device can be seen in the Anderson U.S. Pat. No. 4,382,793 for a device for feeling audio amplifier output, whereby two people can attach belts having electrical chargeable plates for predetermined surface areas in contact with the skin of two participants who can then hold hands. Each can have one channel of a stereo audio output directed towards the electroconductor against the skin, so that both participants can feel the modulated impulses of the sound, as well as hear the output of the speaker. In the Cummins U.S. Pat. No. 4,066,072, and in the Cowan U.S. Pat. No. 3,419,923, environment simulators have been provided for babies after their birth and includes the use of a pressure cushion having an oscillating pressure to simulate the heart beat and may also control the temperature and other conditions in an attempt to recreate, to some degree, some of the conditions that of the womb prior to birth. The Honig U.S. Pat. No. 3,218,638 shows a wireless passage biological telemetering system, while the Hildebrandt U.S. Pat. No. 4,524,774 shows an apparatus and method for the stimulation of human muscles.

In contrast to the prior art, the present invention mounts stereo speakers in a belt forming appropriate acoustical mounting for directing the output directly at the womb and towards an unborn fetus without the sound being heard by others since it is baffled by the belt. The mother may be listening to the same audio source simultaneously with the fetus.

SUMMARY OF THE INVENTION

The present invention relates to a prenatal audio apparatus for directing an audio signal source, such as audio signals generated by a small tape recorder, or the like, towards an unborn fetus. The belt has an inside surface to fit against a persons body adjacent the woman's womb and an outside surface. A belt fastener may be hook and loop material, for adjustably attaching the belt to the person. An audio signal source, such as a battery operated tape recorder, is attachable to the belt and has a pair of headphones for connecting to the users ears. A pair of audio transducers or small speakers are mounted in the belt, having their output side mounted in the belt with the output side facing in the direction of the inside surface against the users skin. The audio transducers are operatively connected to the audio signal source for directing the music or other audio material towards the unborn fetus. The belt may be made of a foamed polymer material, having an outside cloth surface, such as a soft cloth loop material, and may be made of a single piece of material folded over. The folded material may have edges and fold bound together except for areas with edges bound and left open for easy removal of transducers. The folded material also allows a passageway for the conductors from the audio signal transducers to the tape deck to be attached therein. Pockets sewn to the inside of the belt surface holds the transducers in position.

BRIEF DESCRIPTION OF THE DRAWING

Other objects, features and advantages of the present invention will be apparent from the written description and the drawings in which:

FIG. 1 is a perspective of a patient having a prenatal audio apparatus in accordance with the present invention attached thereto;

FIG. 2 is a top plan view of a prenatal audio belt in accordance with the one shown in FIG. 1;

FIG. 3 is a sectional view take on the line 3—3 of FIG. 1;

FIG. 4 is a partial exploded perspective of the opened belt

FIG. 5 is cutaway side elevation of the belt taken on lines 5—5 of FIG. 2; and

FIG. 6 is a partial perspective view of the transducer being inserted into the belt.

DESCRIPTION OF THE PREFERRED EMBODIMENTS

Referring to the drawings, a prenatal audio apparatus 10 is attached to a mother 11 carrying an unborn baby in the womb and has an audio signal source, such as a small miniature tape deck 12, attached to the prenatal audio belt 9. The miniature tape deck 12 is battery operated and has a conductor 13 leading to a pair of headphones 14 for the mother to listen to the material being played by the tape recorder 12. The belt 9 is formed of a foam polymer material 15 having a cloth skin 16 and is elongated flat material folded at the fold 17 to thereby fold a portion 20 over on the foam portion 15. The folded portions may be held together with a hook and loop material 22 and 23 along each elongated edge of the inside of the belt material. The belt material has an audio transducer 25 mounted or sewn into chambers 18 cut out of the foam material 15 and chamber 21 cut out of the foam material 20. The cut out foam material exactly match when the belt material 9 is folded and cut to shape the transducer 25 which is placed therein facing the inside of the belt against the skin of the patient 11, so that the audio source is directed directly towards the womb of the patient 11. Once the audio transducer or audio speaker 25 is placed in the openings or pockets 18 and 21 and a second transducer 26 is placed in the opening 24, the belt can be folded on the fold 17 and sealed with the hook and loop material 22 and 23. The transducers 25 and 26 are connected by a conductor 27 and are further connected by a conductor 28 to the tape recorder 12. The foamed polymer material 15 and 20 advantageously provides cushioning for the belt plus enough thickness to the belt for supporting small audio transducers.

The foamed polymer material forms a cavity for improving the output of the audio transducers 25 and 26 while assisting in preventing the audio source from being heard by anyone near the patient 11. The belt 10 has hook and loop material 30 on one end thereof and hook and loop material 31 on the other end thereof so that it can be quickly attached to a patient 11 and adjust for different patients and for different degrees of pregnancy. The cloth 16 may also be made of a soft loop material for connection with the hook material. The audio material is directed against the skin directly at the fetus in the womb of the patient 11 while being simultaneously directed towards the earphones 14 to produce stereo in both the mother and the unborn fetus. The audio source can be music or specially selected music found to soothe the unborn fetus and may also include specially designed learning materials placed on tapes for the tape recorder 12, or the parents voices recorded on tapes.

It should be clear at this point that the prenatal audio apparatus has been provided which has a design for supporting stereo or mono audio transducers, special cavities for directing the audio signal towards the unborn fetus and as well as two headphones on the patient. It should, however, be clear that the present invention is not to be construed as limited to the forms shown, which are to be considered illustrative rather then restrictive.

I claim:

1. A prenatal audio apparatus comprising in combination:
    a belt having an inside surface to fit against a person's body and an outside surface;
    a belt fastener means for adjustably attaching the belt to a person;
    a tape recorder audio signal source attachable to said belt;
    at least one audio transducer having an output side, said audio transducer being mounted in said belt with the output side facing in the direction of the inside surface of said belt, and said audio transducer being operatively connected to said tape recorder audio signal source, whereby audio signals from a tape recorder are directed into a person's body.

2. A prenatal audio apparatus in accordance with claim 1 in which said belt is formed of a foamed polymer material having audio transducer pockets formed therein.

3. A prenatal audio apparatus in accordance with claim 2 in which said belt foamed polymer material has a cloth surface thereon.

4. A prenatal audio apparatus in accordance with claim 3 in which said belt includes a foamed polymer material folded along an elongated center line and attached with elongated VELCRO members.

5. A prenatal audio apparatus in accordance with claim 4 in which said belt foamed polymer material has a pair of pockets formed therein which are folded to fit over each other to form an audio transducer cavity.

6. A prenatal audio apparatus in accordance with claim 1 in which a pair of headphones may be connected to the tape recorder audio signal source for simultaneously listening by, a person using said prenatal audio apparatus.

7. A prenatal audio apparatus in accordance with claim 6 in which a pair of audio transducers are mounted in said belt to provide stereo from said transducers against a person's skin and towards the person's womb.

* * * * *